(12) United States Patent
Lee et al.

(10) Patent No.: US 8,617,485 B2
(45) Date of Patent: Dec. 31, 2013

(54) SENSOR STRIP DEVICE FOR MEASURING PROTEIN IN THE BLOOD

(75) Inventors: Hyo Geun Lee, Suwon-si (KR); Hyo Lim Park, Yongin-si (KR); Eun Sun Song, Suwon-si (KR); Byung Hak Song, Suwon-si (KR)

(73) Assignee: SD Biosensor, Inc., Suwon (KR)

( * ) Notice: Subject to any disclaimer, the term of this patent is extended or adjusted under 35 U.S.C. 154(b) by 0 days.

(21) Appl. No.: 13/583,628

(22) PCT Filed: Mar. 14, 2011

(86) PCT No.: PCT/KR2011/001775
§ 371 (c)(1),
(2), (4) Date: Sep. 8, 2012

(87) PCT Pub. No.: WO2011/112062
PCT Pub. Date: Sep. 15, 2011

(65) Prior Publication Data
US 2012/0329145 A1    Dec. 27, 2012

(30) Foreign Application Priority Data

Mar. 12, 2010 (KR) .................. 10-2010-0022340

(51) Int. Cl.
*G01N 33/49* (2006.01)

(52) U.S. Cl.
USPC ........... 422/401; 422/400; 422/408; 422/412; 422/68.1; 422/69; 422/503

(58) Field of Classification Search
USPC ........... 422/400, 401, 408, 412, 68.1, 69, 503
See application file for complete search history.

(56) References Cited

U.S. PATENT DOCUMENTS 6,040,195 A * 3/2000 Carroll et al. ................. 436/514

* cited by examiner

*Primary Examiner* — Monique Cole
(74) *Attorney, Agent, or Firm* — LRK Patent Law Firm

(57) ABSTRACT

A sensor strip apparatus includes: a top plate having an entrance opening downward and a joint formed downward; a pad section including a support having a window opening downward, a reaction pad attached to the window of the support and reacting with a specimen, first and second hemolysis inhibition pads attached to the reaction pad to filter hemocytes from the specimen, a specimen pad attached to the first and second hemolysis inhibition pads to diffuse the specimen crosswise, and an adhesive film attached to the support around the first and second hemolysis inhibition pads to increase adhesion strength of the specimen pad; and a bottom plate having a second joint forcibly coupled with to the joint of the top plate, and a window configured to indentify the reaction pad through the window of the support.

15 Claims, 6 Drawing Sheets

SENSOR STRIP DEVICE FOR MEASURING PROTEIN IN THE BLOOD

TECHNICAL FIELD

The present invention relates generally to a senior strip apparatus for colorimetry to measure protein from blood, more particularly to a sensor strip configured to minimize variation on values of measurement.

BACKGROUND ART

Inspecting a specific value from a specimen such as blood is generally carried out by way of measurement with testing papers, i.e. sensor strips (biosensor strips). For example, measuring blood glucose proceeds in the course as follows. First, a finger is inserted into a glucose monitor and then blood is taken from the finger. As this blood is automatically sucked into the inlet of a sensor strip when it arrives at the sensor strip pinned up the glucose monitor, a resultant glucose value is expressed on the screen of the monitor.

For the strip structure, a unit strip has been usually fabricated in the following manner. A plastic housing is formed of top and bottom plates. On the plastic housing are overlapped a nitrocellulose membrane, a hemolysis inhibition pad and a sampling pad in order. Then, after folding and inserting the top plate in a hole pin, it is joined by means of an electric iron to complete the structure. However, such an integrated strip structure is disadvantageous to production yield and consumes a large quantity of blood, mostly causing irregular variations on values of measurement due to compressive gaps between the top and bottom plates.

Meanwhile, there has been a multi strip with separated lop and bottom plates of the plastic housing, in which a nitrocellulose membrane and a hemolysis inhibition pad are laminated on a polypropylene plate (backing plate) having circular punches at an inspection point. On the laminated structure, sampling pads are layered on the plastic housing in order and the top plate is inserted to join therewith. Then, a sampling hole is formed to be wet with blood at once so as to measure three items of total cholesterol high-density lipoprotein (HDL) and triglyceride (TG). But, it could generate variations on values of measurement, depending upon points to which blood is dropping, in a large size of the sampling hole.

DISCLOSURE

Technical Problem

Accordingly, the present invention is directed to provide a sensor strip apparatus for measuring proteins from blood, including a housing structure advantageous us minimizing variations of measurement and improving a product yield in mass production.

The present invention is also directed to provide a sensor strip apparatus for measuring proteins from blood, including means helpful to minimizing variations of measurement as well as enabling even a small quantity of specimen to arrive regularly and quickly at respective reaction pads in a strip structure for inspecting multiple properties.

Technical Solution

In an embodiment according to the present invention, a sensor strip apparatus for measuring protein from blood may be comprised of a top plate having an entrance opening downward and a joint formed downward; a pad section comprising a support having a window opening downward, a reaction pad attached to the window of the support and reacting with a specimen, first and second hemolysis inhibition pads attached to the reaction pad to filter hemocytes from the specimen, a specimen pad attached to the first and second hemolysis inhibition pads to diffuse the specimen crosswise, and an adhesive film attached to the support around the first and second hemolysis inhibition pads to increase adhesion strength of the specimen pad; and a bottom plate having a second joint forcibly coupled with to the joint of the top plate, and a window configured to indentify the reaction pad through the window of the support.

The apparatus may further comprise a protruded compression plate formed on a lower side of the top plate to apply uniform pressure to the pad section while fabricating the apparatus.

In another embodiment, a sensor strip apparatus for measuring protein from blood may be comprised of: a top plate having an entrance opening downward and a joint formed downward; a pad section including a support having lengthwise three windows opening downward, a first reaction pad attached to a first one of the three windows of the support and reacting with a specimen to measure total cholesterol, a second reaction pad attached to a second one of the three-windows of the support and reacting with the specimen to measure high-density liproprotein, a third reaction pad attached to a third one of the three windows of the support and reacting with a specimen to measure triglyceride, first and second hemolysis inhibition pads attached to the reaction pad to filter hemocytes from the specimen, a specimen pad attached to the first and second hemolysis inhibition pads to diffuse the specimen crosswise, and an adhesive film attached to the support around the first and second hemolysis inhibition pads to increase adhesion strength of the specimen pad; and a bottom plate having a second joint forcibly coupled with to the joint of the top plate, and windows configured to indentify the reaction pads respectively through the windows of the support.

In this embodiment, the apparatus may further comprise a protruded compression plate formed on a lower side of the top plate to apply uniform pressure to the pad section, while fabricating the apparatus.

In the embodiments of the present invention, the apparatus may further comprise a fluid channel configured in a narrow ditch type along a length direction of the compression plate in the top plate.

The apparatus may also further comprise a strip sue formed on the bottom plate, corresponding to the pad section in shape, to render the pad section to be settled therein when fabricating the apparatus.

The adhesive film may have a thickness between 0.4 mm and 0.6 mm.

The apparatus may further comprise a wing configured to extend by width toward left and right along the length direction of the bottom plate.

Additionally, the apparatus may further comprise a handle formed extending lengthwise in the bottom plate.

And the apparatus may further comprise a slip-resistive rib grooved at a right angle to a direction of insertion.

A further understanding of the nature and advantages of the present invention herein may be realized by reference to the remaining portions of the specification and the attached drawings.

Advantageous Effects

Front the structural feature of the present invention, a sensor strip apparatus for measuring a single property, which is formed such that: a plastic housing is divided into top and bottom plates; a nitrocellulose membrane, a hemolysis inhibition pad and a sampling pad are laminated to be laid in the plastic housing; and the top and bottom plates are inserted into a pinhole to join with each other, is advantageous to increasing a production yield in mass production and minimizing variations of measurement by reducing compressional gaps between the top and bottom plates.

Moreover, this sensor strip apparatus for measuring multiple properties from blood is suitable for improving a product yield in mass production, minimizing variations on values of measurement and enabling even a small quantity of specimen to arrive regularly and quickly at reaction pads respectively through a fluid channel. Consequently, the regularity of compressional gaps and the rapid arrival of specimen make the measurement more precisely and accurately.

BEST MODE

Figure 1:
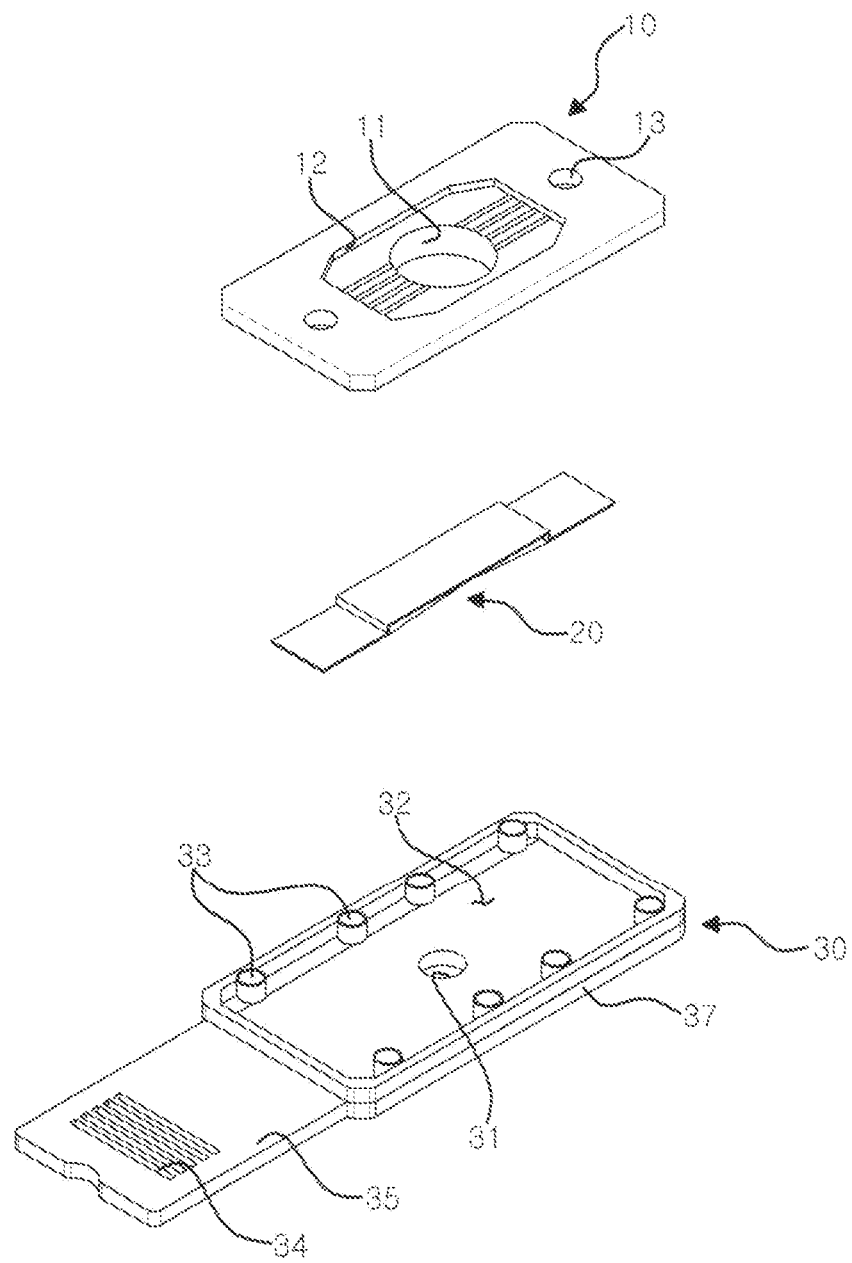
FIG. 1 is a disassembled perspective view illustrating an apparatus for measuring a single property from blood.

Hereinafter, preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scone of the present invention to those skilled in the art. In the description, terms indicating orientations, e.g. 'up', 'down', 'left' and 'right', may be understood that they are referred as noticed in the drawings. Like reference marks refer to similar elements.

Figure 6:
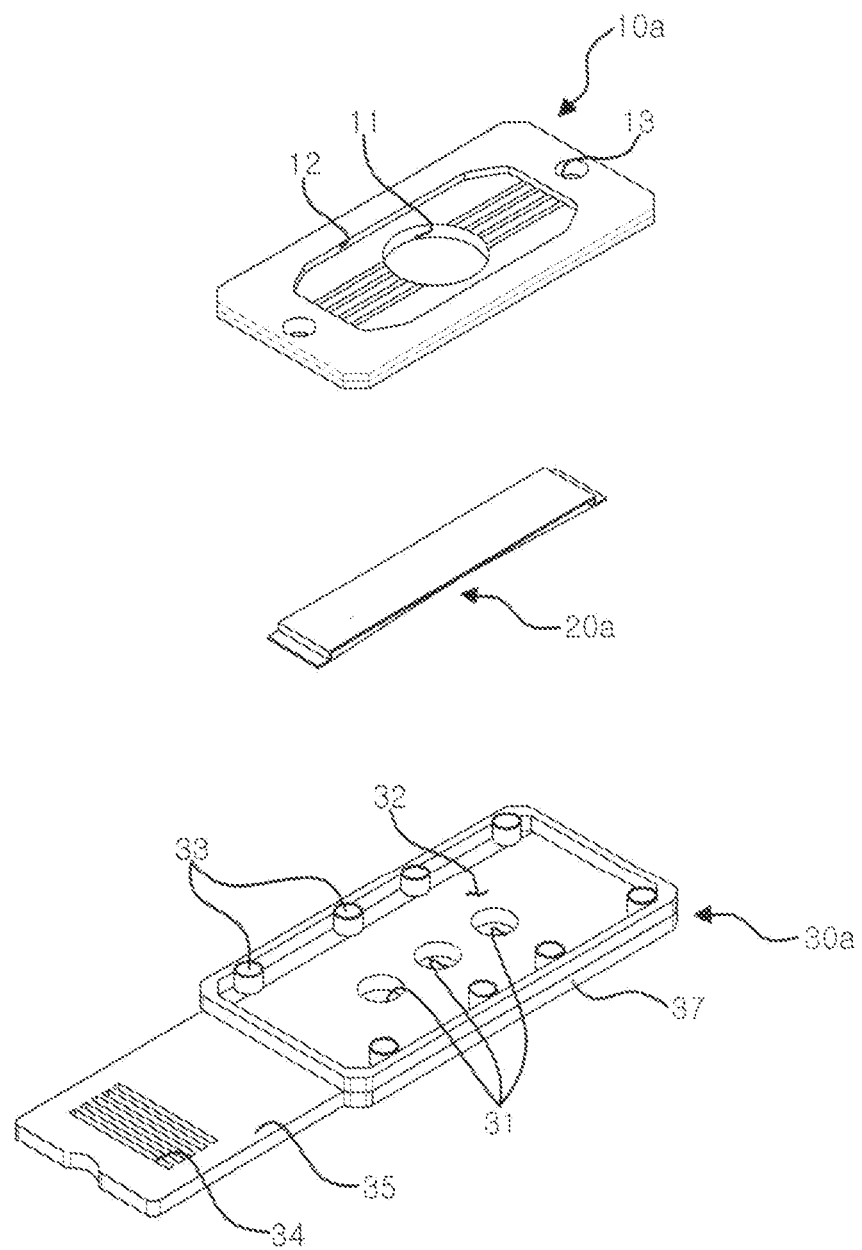
FIG. 6 is a disassembled perspective view illustrating an apparatus for measuring multiple properties from blood.

A sensor strip apparatus according to the present invention, as illustrated in FIGS. 1 and 6, is formed to include a housing that is composed of top and bottom plates 10 and 30, and pad 20 disposed between top and bottom plates 10 and 30. Hereinafter will be detailed two kinds of embodiments: one (as referred to as Embodiment 1) for measuring a single property from blood; and the other (as referred to as Embodiment 2) for measuring multiple properties from blood, in sequence.

Embodiment 1

This embodiment employs one reaction pad for measuring a single property from blood as illustrated in FIG. 1.

FIG. 1 shows a disassembled perspective of a sensor strip apparatus for single property measurement, which is organized of top plate 10, pad section 20 and bottom plate 30.

Top plate 10 is made up to have an entrance into which a specimen can be thrown, and a joint at the bottom.

Entrance 11 is formed of a hole to open top plate 10 downward. A specimen of blood thrown into the entrance 11 arrives at specimen pad 26 of pad section 20 which is described later. As small as a diameter of entrance 11 is, a variation of measurement becomes smaller every measurement because the specimen is distributed at a constant region on specimen pad 26 with higher uniformity.

Meanwhile, in case of coupling this apparatus with an additional measuring device (not shown), guiding rib 12 and grooves 13 may be formed therein to enhance an insertional sense and fixation force.

Guiding rib 12 is provided to offer an insertional sense and strengthen fixation force to left and right when the sensor strip apparatus joins with an additional measurement device (not shown). And grooves 13 are formed to be correspondent with prominences which may be built in the additional measurement device, enhancing an insertional sense and fixation force when the sensor strip apparatus joins with an additional measurement device. On the other hand in an embodiment, the apparatus may be even comprised of prominences while the additional measurement device has grooves.

Compression plate 14 is set on a lower side of top plate 10. Compression plate 14 is formed in a protruded plane higher than the circumference, functioning to apply pressure uniformly to pad section 20 when top plate 10 joins with bottom plate 30, securing reproducibility of a specimen.

In this embodiment, prominences 15 are formed at the lower side of top plate 10 in the number of eight. These prominences 15 joins each with grooves 33 of bottom plate 30 which will be described hereinafter, enabling top and bottom plates 10 and 30 to be assembled to compress a specimen.

Figure 2:
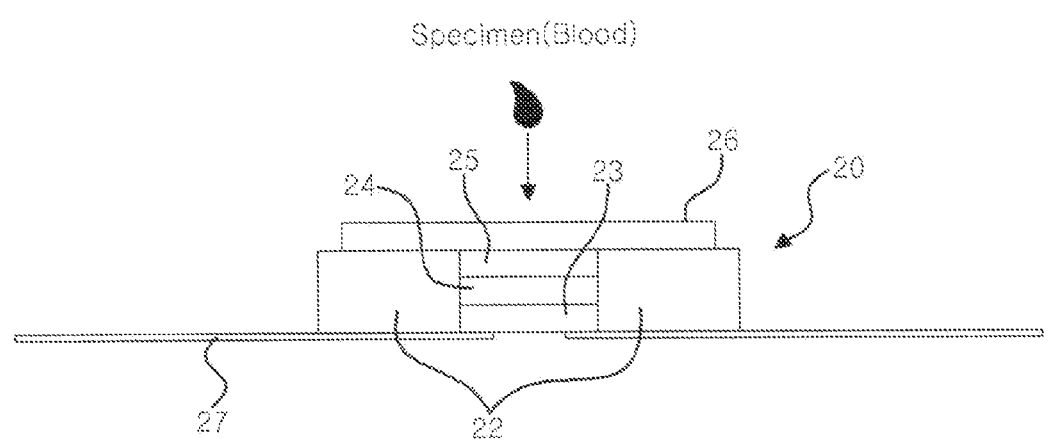
FIG. 2 is a lengthwise sectional view illustrating a pad section of the apparatus shown in FIG. 1.
Figure 3:
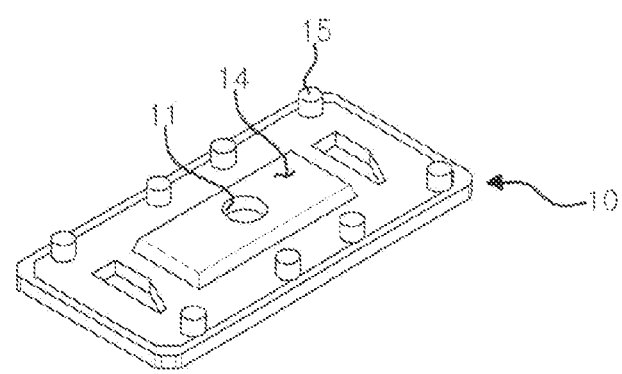
FIG. 3 is a lower perspective view illustrating a top plate of the apparatus shown in FIG. 1.

FIG. 2 is a lengthwise sectional view illustrating a pad of the apparatus shown in FIG. 1, and FIG. 3 is a lower perspective view illustrating a top plate of the apparatus shown in FIG. 1.

Now top plate 10 will be described with reference to FIGS. 1 and 3.

Entrance 11 is formed of a hole to open top plate 10 downward. Into entrance 11, a specimen of blood is thrown to arrive at specimen pad 26 of pad section 20. Here, a smaller diameter is helpful to higher uniformity in arrival and diffusion of the specimen at specimen pad 26, hence reducing inspective variations every measurement.

In the meantime, for the purpose of increasing insertional sense and fixation force when this apparatus joins with the additional measurement device (not shown), guiding rib 12 and grooves 13 may be formed therein.

In this structure, guiding rib 12 is provided to offer an insertional sense and strengthen fixation force to left and right sides when joining the sensor strip apparatus with the additional measurement device (not shown). And grooves 13 are formed to be correspondent with prominences which may be provided in the additional measurement device, enhancing an insertional sense and fixation force when the sensor strip apparatus joins with an additional measurement device. Reversely, the apparatus may be even equipped with prominences while the additional measurement device has grooves.

On the lower side of top plate 10, compression plate 14 is formed in a protruded plane higher than the circumference, applying pressure uniformly to pad section 20 when top plate 10 joins with bottom plate 30, effective in enhancing reproducibility of a specimen.

Prominences 15, according to this embodiment, are formed at the lower side of top plate 10 in the number of eight. These prominences 15 joins each with grooves 33 of bottom plate 30 which will be described hereinafter, permitting top and bottom plates 10 and 30 to be assembled for compressing a specimen.

Figure 4:
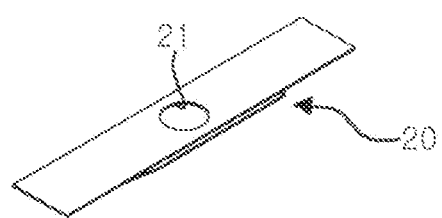
FIG. 4 is a lower perspective view illustrating the pad section of the apparatus shown in FIG. 1.

Now will be described pad section 20 in conjunction with FIGS. 1, 2 and 4. FIG. 2 shows a lengthwise cut of pad section 20 and FIG. 4 shows a lower perspective of pad section 20.

Support 27 is made of plastic. On support 27, glue is partly spread to permit a hemolysis inhibition pad to be attached thereto and a release paper is pasted thereon. In order to obviate interference at a part of measurement while inspecting, strip window 21 is formed by punching in a circular pattern. A user is able to identify a color of reaction pad, after arrival and reaction of a specimen at the reaction pad, through strip window 21.

Specimen pad 26 is set to make a sample of blood diffused rapidly and uniformly to arrive at second hemolysis inhibition layer 25 without differences when it drops into entrance 11.

Adhesive film 22 is made of an expanded double-side tape. In practice, laminating the specimen pad 26 on support 27 is not easy due to a thickness by hemolysis inhibition pads 24 and 25 and reaction pad 23 which are previously laid thereon. In order to make specimen pad 26 laminated in convenience, adhesive film 22 is provided to both sides of the previously laminated pads 23~25. During this, adhesive film 22 may be used with a double-side tape in a thickness of 0.4 mm~0.6 mm. If adhesive flint 22 is less than the minimum thickness of the pads 23~25, a correction effect for height could be insufficient to make the lamination not easy. If adhesive film 22 is more than the maximum thickness 0.6 mm of the pads 23~25, an excessive correction could incur to rather make the lamination inconvenient.

Hemolysis inhibition pads, 24 and 25, are composed of first and second layers with a material capable of filtering hemocytes, fully straining hemocytes from a blood sample not to go down to a nitrocellulose membrane that is a reaction layer in measuring HDL, the blood sample is treated in advance to make a solution from which low-density lipoprotein (LDL) can be extracted.

Reaction pad (a nitrocellulose membrane layer) 23 as a layer reacting with cholesterol or TG of blood is formed by pouring a mixture of enzyme and substrate into the nitrocellulose layer and drying the poured nitrocellulose layer, being changed to be dark in color by heavier concentration of cholesterol or TG while reacting with blood. Such a change of concentration from the reaction pad can be found out through a colorimeter (not shown).

Hereinafter will be described a process for fabricating pad section 20. This process is composed of three steps of forming an immobilized enzyme nitrocellulose strip; forming a strip to which the hemolysis inhibition pad and the specimen pad are attached; and forming an analyzing device.

In the step of forming a strip with a immobilized enzyme nitrocellulose membrane (reaction pad 23), first total cholesterol HDL or TG lyase according to a specimen to be inspected is diluted a buffer solution and then the nitrocellulose membrane is deposited and uniformly wet in the diluted solution. After that, the wet nitrocellulose membrane is dried out for 30 minutes under 40° C. in a thermostat, thereby immobilizing the enzyme therein. Then, this nitrocellulose membrane 23 is cut out in the width of 5 mm and attached on strip window 21 after removing the release paper from the support on which the glue is spread.

Next, in the step of forming a strip with the hemolysis inhibition pad and the specimen pad, first an expanded double-side tape is laminated on around the strip to which nitrocellulose membrane 23 is attached. After laminating first and second hemolysis inhibition pads, which are cut out in width of 5 mm, between them, adhesive film 22 is formed by means of a double-side tape. Then specimen pad 26 is attached on the adhesive film 22.

Finally, in the step of completing an analyzing device, the strip fabricated from the former steps is cut out in the width of 5 mm and then compressed by a housing cover which is settled inside of a strip guiding pin of the housing.

Figure 5:
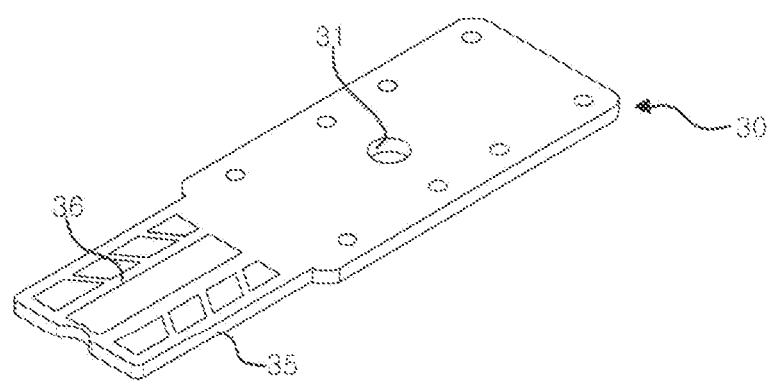
FIG. 5 is a lower perspective view illustrating a bottom plate of the apparatus shown in FIG. 1.

Now will be described bottom plate 30 in conjunction with FIGS. 1 and 5, FIG. 5 shows a lower perspective view of bottom plate 30.

As like top plate 10, bottom plate 30 is made of plastic and coupled with top plate 10 to form the housing.

Bottom window 31 is formed in a type of through hole to overlap with strip window 21. Colorimetry can be conducted by monitoring a change of color from reaction pad 23 through strip window 21 and bottom window 31.

Strip site 32 is formed dependent on a shape and size of pad section 20, rendering pad section 20 to be settled in a small interval.

Grooves, 33, are forcibly combined with prominences 15 (refer to FIG. 3) to support a housing structure by compressively joining top and bottom plates 10 and 30 with each other. Otherwise, it is also permissible to oppositely change grooves 33 and prominences 15 in location. A pair of groove 33 and prominence 15 can be called a joint.

Handle 35 id formed by extending its end along the length of the bottom plate, making the sensor strip apparatus easily inserted into a colorimeter. In an embodiment, handle 35 may include slip-resistive rib 34, which prevents the apparatus from sliding when it is inserted into the colorimeter, and reinforcing rib 36 to reduce stress thereat.

Wing 37 is extended to left and right by the lengthwise direction of bottom plate 30, a width of which is larger than the circumference. Wing 37 functions to prevent interference by external light, contributing more accurate colorimetry.

By joining grooves 33 with prominences 15 (refer to FIG. 3) of top plate 10 after settling pad section 20 on strip site 32 of bottom plate 30, the sensor strip apparatus is completely fabricated.

Embodiment 2

As illustrated in FIG. 6, Embodiment 2 is about a sensor strip apparatus for measuring multiple properties from blood, providing three of reaction pads 23a~23c therein while entrance 11 is one.

Figure 8:
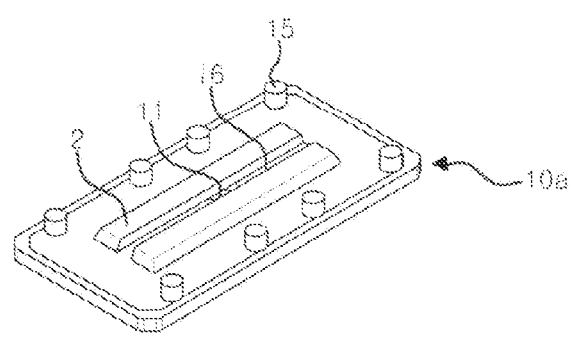
FIG. 8 is a lower perspective view illustrating a top plate of die apparatus shown in FIG. 6.
Figure 9:
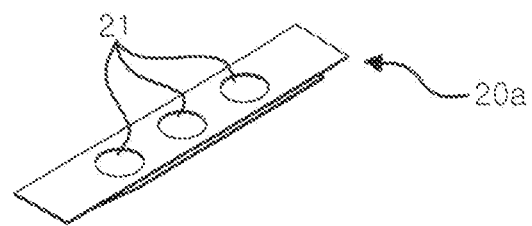
FIG. 9 is a lower perspective view illustrating the pad section of the apparatus shown in FIG. 6.

Referring to FIGS. 6 and 8, top plate 10a will be first described hereinafter. FIG. 8 shows a lower perspective of top plate 10a.

Top plate 10a according to Embodiment 2 is different from the top plate 10 of Embodiment 1 in the feature that as illustrated in FIG. 8 fluid channel 16 may be formed in a narrow ditch along the length direction of compression plate 14. Fluid channel 16 enables a specimen (blood) to be distributed along the length direction by capillary action so as to arrive at reaction pads 22a~22c.

Figure 7:
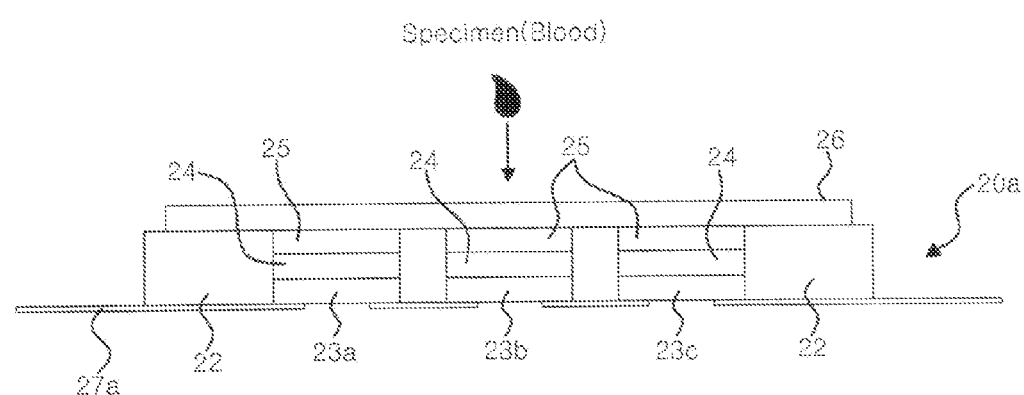
FIG. 7 is a lengthwise sectional view illustrating a pad section of the apparatus shown in FIG. 6.

Referring to FIGS. 6, 7 and 8, pad section 20a will be now described. FIG. 7 illustrates a lengthwise cut of pad section 20 and FIG. 8 illustrates a lower perspective of pad section 20a.

Different from pad section 20 of Embodiment 1, pad section 20a is shown as that strip window 21 is provided to each of reaction pads 22a~22c as illustrated in FIG. 8.

Internally, referring to FIG. 7, three pairs of reaction pad 22a and hemolysis inhibition pads 24 and 25 are arranged, spatially isolated, along the length direction of pad section 20a, each reaction pad, 22a, 22b or 22c, as aforementioned, immobilized by independently diluting total cholesterol, HDL, and TG lyase in buffer solutions, depositing and uniformly wetting nitrocellulose membranes respectively in the solution, and drying it for 30 minutes under 40° C. in a thermostat. These three reaction pads 22a~22c are each used for fabricating pad section 20a.

The pairs of reaction pads 22a~22c and hemolysis inhibition pads 24 and 25 are then laminated on strip windows 21 respectively formed in supports 27a.

Figure 10:
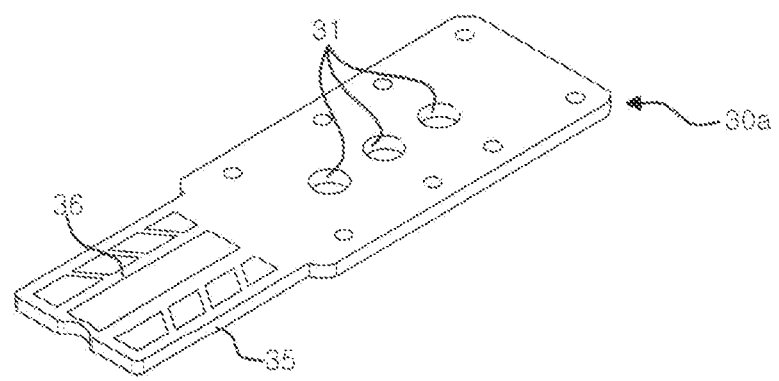
FIG. 10 is a lower perspective view illustrating a bottom plate of the apparatus shown in FIG. 6.

Now bottom plate 30a will be described with reference to FIGS. 6 and 10. FIG. 10 illustrates a lower perspective of bottom plate 30a.

Bottom plate 30a according to Embodiment 2 is different front the bottom plate 30 (refer to FIG. 5) of Embodiment 1 in the number of bottom windows 31. In this embodiment, bottom plates 30a are formed to overlap three bottom plates 31, in total for example, respectively with strip windows 21 that have been built in support 27a of pad section 20a when fabricating the sensor strip apparatus.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

INDUSTRIAL APPLICABILITY

The present invention is applicable to sensor strip apparatus used in colorimetry for measuring protein from a specimen of blood, especially effective in raising yields of mass production, minimising variations on values of measurements regularizing congressional gaps, improving inspection for uniform and rapid arrival of specimen to the reaction pad.

The invention claimed is:

1. A sensor strip apparatus for measuring protein from blood, comprising:
a top plate having an entrance opening downward and a joint formed downward;
a pad section comprising: a support having a window opening downward; a reaction pad attached to the window of the support and reacting with a specimen; first and second hemolysis inhibition pads attached to the reaction pad to filter hemocytes from the specimen; a specimen pad attached to the first and second hemolysis inhibition pads to diffuse the specimen crosswise; and an adhesive film attached to the support around the first and second hemolysis inhibition pads to increase adhesion strength of the specimen pad; and
a bottom plate having a second joint forcibly coupled with to the joint of the top plate, and a window configured to indentify the reaction pad through the window of the support.

2. The apparatus as set forth in claim 1, further comprising a protruded compression plate formed on a lower side of the top plate to apply uniform pressure to the pad section while fabricating the apparatus.

3. A sensor strip apparatus for measuring protein from blood, comprising:
a top plate having an entrance opening downward and a joint formed downward;
a pad section comprising: a support having lengthwise three windows opening downward; a first reaction pad attached to a first one of the three window of the support and reacting with a specimen to measure total cholesterol; a second reaction pad attached to a second one of the three window of the support and reacting with the specimen to measure high-density liproprotein; a third reaction pad attached to a third one of the three window of the support and reacting with a specimen to measure triglyceride; first and second hemolysis inhibition pads attached to the reaction pad to filter hemocytes from the specimen; a specimen pad attached to the first and second hemolysis inhibition pads to diffuse the specimen crosswise; and an adhesive film attached to the support around the first and second hemolysis inhibition pads to increase adhesion strength of the specimen pad; and
a bottom plate having a second joint forcibly coupled with to the joint of the top plate, and windows configured to indentify the reactions pad respectively through the windows of the support.

4. The apparatus as set forth in claim 3, further comprising a protruded compression plate formed on a lower side of the top plate to apply uniform pressure to the pad section while fabricating the apparatus.

5. The apparatus as set forth in claim 4, further comprising a fluid channel configured in a narrow ditch type along a length direction of the compression plate in the top plate.

6. The apparatus as set forth in claim 1, further comprising a recessed strip site formed on the bottom plate, corresponding to the pad section in shape, to render the pad section to be settled therein while fabricating the apparatus.

7. The apparatus as set forth in claim 1, wherein the adhesive film has a thickness between 0.4 mm and 0.6 mm.

8. The apparatus as set forth in claim 1, further comprising a wing configured to extend by width toward left and right along the length direction of the bottom plate.

9. The apparatus as set forth in claim 1, further comprising a handle formed extending lengthwise in the bottom plate.

10. The apparatus as set forth in claim 9, further comprising a slip-resistive rib grooved at a right angle to a direction of insertion.

11. The apparatus as set forth in claim 3, further comprising a recessed strip site formed on the bottom plate, corresponding to the pad section in shape, to render the pad section to be settled therein while fabricating the apparatus.

12. The apparatus as set forth in claim 3, wherein the adhesive film has a thickness between 0.4 mm and 0.6 mm.

13. The apparatus as set forth in claim 3, further comprising a wing configured to extend by width toward left and right along the length direction of the bottom plate.

14. The apparatus as set forth in claim 3, further comprising a handle formed extending lengthwise in the bottom plate.

15. The apparatus as set forth in claim 14, further comprising a slip-resistive rib grooved at a right angle to a direction of insertion.

* * * * *